United States Patent
Wang

(10) Patent No.: US 11,424,416 B2
(45) Date of Patent: Aug. 23, 2022

(54) LIGHT THERMALLY ACTIVATED DELAYED FLUORESCENCE (TADF) MATERIAL, PREPARING METHOD THEREOF, AND ELECTROLUMINESCENT DEVICE

(71) Applicant: WUHAN CHINA STAR OPTOELECTRONICS SEMICONDUCTOR DISPLAY TECHNOLOGY CO., LTD., Hubei (CN)

(72) Inventor: Yanjie Wang, Hubei (CN)

(73) Assignee: WUHAN CHINA STAR OPTOELECTRONICS SEMICONDUCTOR DISPLAY TECHNOLOGY CO., LTD., Hubei (CN)

( * ) Notice: Subject to any disclaimer, the term of this patent is extended or adjusted under 35 U.S.C. 154(b) by 443 days.

(21) Appl. No.: 16/499,272

(22) PCT Filed: May 27, 2019

(86) PCT No.: PCT/CN2019/088469
§ 371 (c)(1),
(2) Date: Sep. 29, 2019

(87) PCT Pub. No.: WO2020/220418
PCT Pub. Date: Nov. 5, 2020

(65) Prior Publication Data
US 2020/0343454 A1 Oct. 29, 2020

(30) Foreign Application Priority Data
Apr. 29, 2019 (CN) .......................... 201910354664.0

(51) Int. Cl.
H01L 51/50 (2006.01)
H01L 51/00 (2006.01)
(Continued)

(52) U.S. Cl.
CPC ........ *H01L 51/0072* (2013.01); *C07D 417/10* (2013.01); *C09K 11/06* (2013.01);
(Continued)

(58) Field of Classification Search
None
See application file for complete search history.

(56) References Cited

U.S. PATENT DOCUMENTS

2019/0334097 A1* 10/2019 Sugawara ................. G09F 9/30

* cited by examiner

*Primary Examiner* — Gregory D Clark
(74) *Attorney, Agent, or Firm* — Mark M. Friedman

(57) ABSTRACT

The present invention provides a thermally activated delayed fluorescent material, a method for preparing the same, and an electroluminescent device including a compound consisting of a receptor A and a donor D, the compound having a molecular structure of D-A shown in Formula 1:

D-A      Formula 1

(Continued)

wherein the receptor A is selected from any one of the following structural formulas:
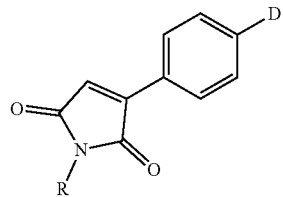
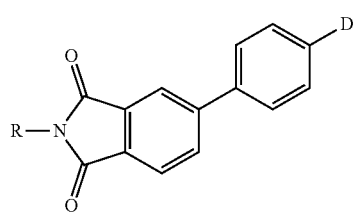
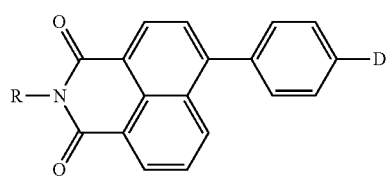
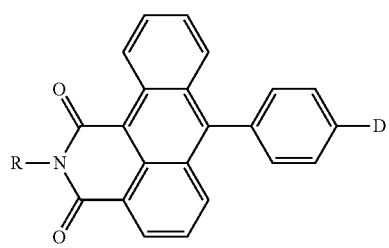
wherein R is selected from any one of the following structural formulas:
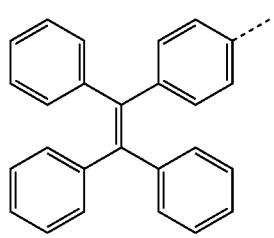
-continued
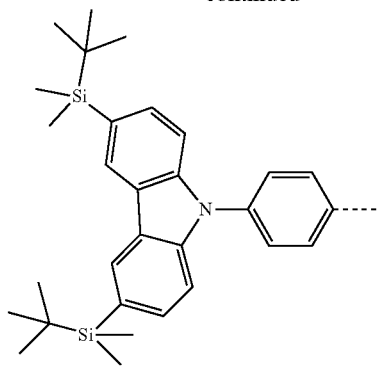
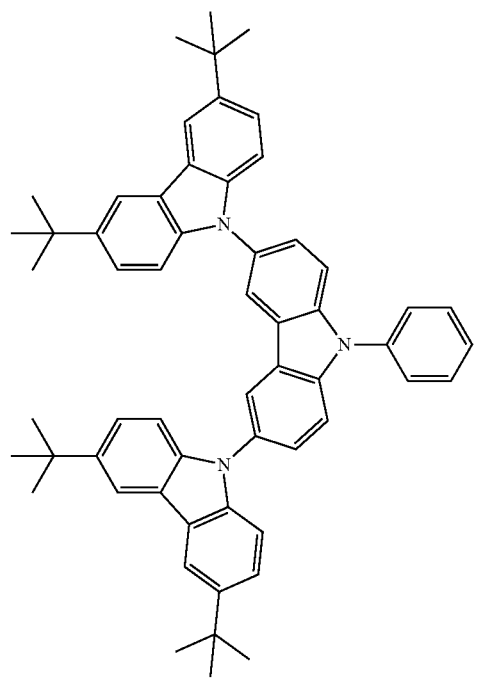
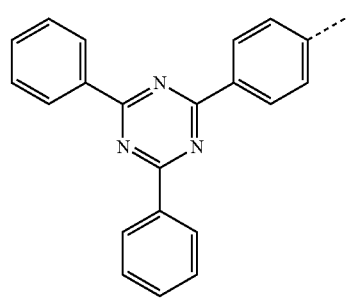

-continued
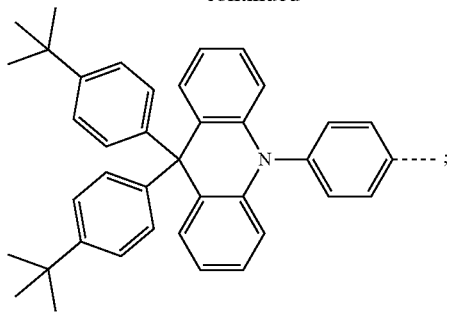
and
the donor D is selected from any one of the following structural formulas:
-continued
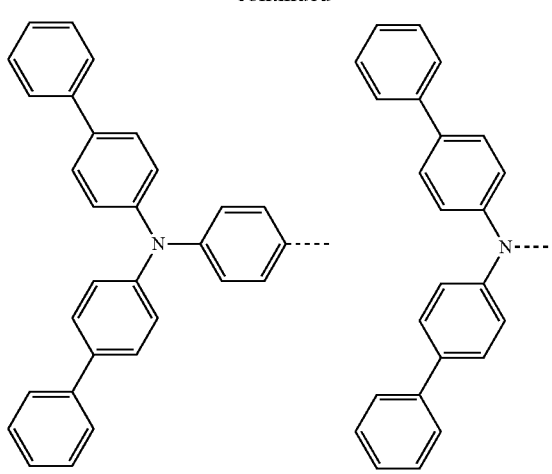
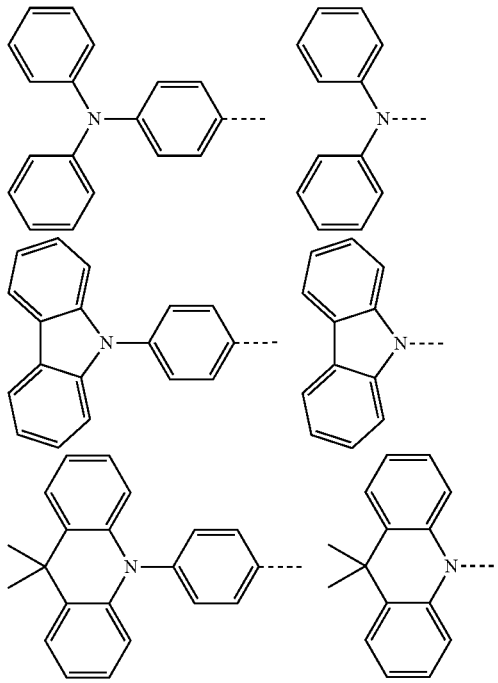
D
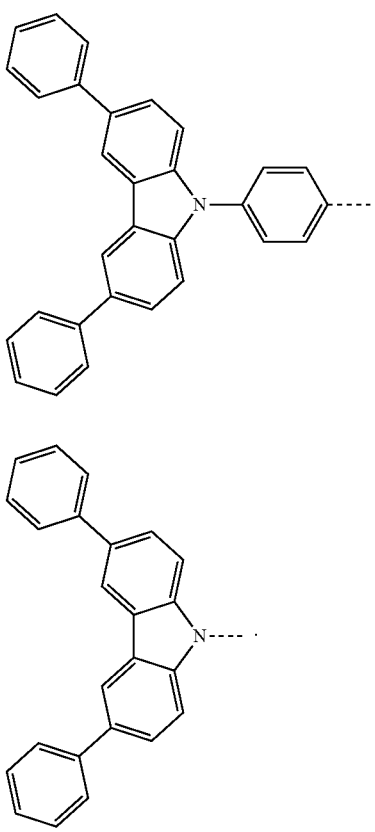
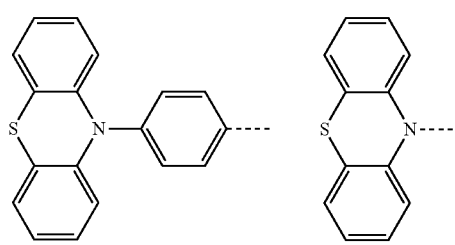
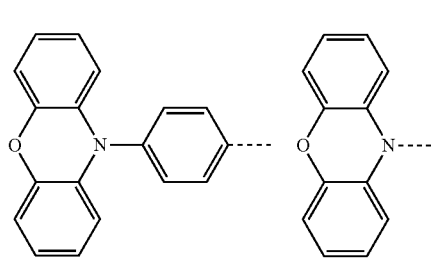
10 Claims, 2 Drawing Sheets
(51) Int. Cl.
  *C09K 11/06*   (2006.01)
  *C07D 417/10*   (2006.01)
  *H01L 51/52*   (2006.01)
  *H01L 51/56*   (2006.01)

(52) U.S. Cl.
CPC ............ *C09K 2211/1007* (2013.01); *C09K 2211/1018* (2013.01); *H01L 51/0003* (2013.01); *H01L 51/0025* (2013.01); *H01L 51/5016* (2013.01); *H01L 51/5056* (2013.01); *H01L 51/5072* (2013.01); *H01L 51/5088* (2013.01); *H01L 51/5206* (2013.01); *H01L 51/5221* (2013.01); *H01L 51/56* (2013.01)

adding a compound A-X and a compound D-H to a solution containing an alkali, wherein X is a halogen, and A is any one of the following structural formulas:

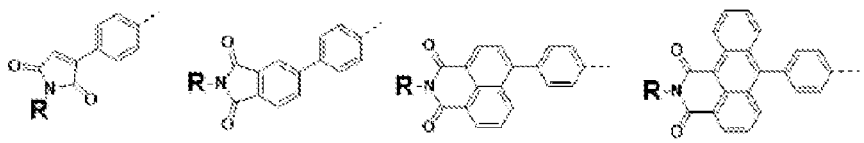

where R is selected from any one of the following structural formulas:

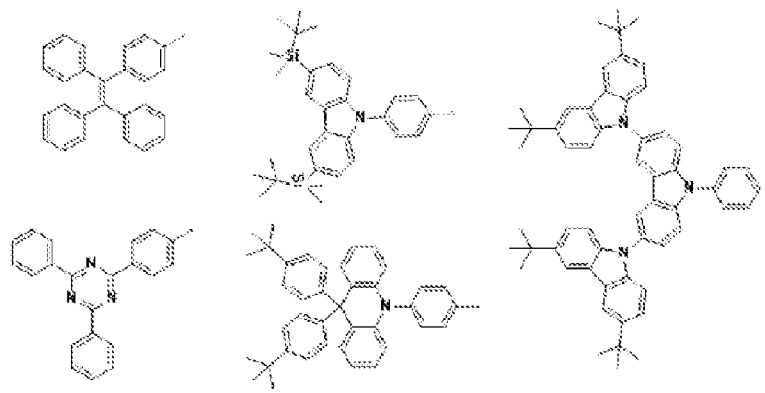

and D is any one of the following structural formulas:

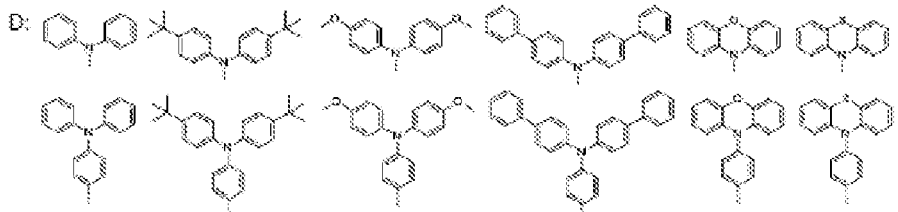

↓ adding a palladium catalyst to the solution containing the alkali under an inert gas for reaction at a first temperature for a first period of time to obtain a reaction solution; — S20

↓ cooling the reaction solution to a second temperature to obtain a mixture; — S30

↓ separating the thermal activated delayed fluorescent material from the mixture, wherein the thermal activated delayed fluorescent material includes a compound consisting of a receptor A and a donor D, the compound having a molecular structure shown in Formula 1: D-A. — S40

FIG. 1

LIGHT THERMALLY ACTIVATED DELAYED FLUORESCENCE (TADF) MATERIAL, PREPARING METHOD THEREOF, AND ELECTROLUMINESCENT DEVICE

BACKGROUND OF INVENTION

Field of Invention

The present invention relates to the field of display technologies, and in particular, to a thermally activated delayed fluorescent (TADF) material, a method for preparing the same, and an electroluminescent device.

Description of Prior Art

It is known that organic light-emitting diodes (OLEDs) have attracted attention from many researchers, due to their huge application prospects and advantages, such as self-illumination without the need for a backlight, high luminous efficiency, wide viewing angles, fast response speed, a large temperature adaptation range, relatively simple production and processing techniques, low driving voltage, low energy consumption, lightness, thinness, flexibility, and so on.

A conventional OLED display device generally includes a substrate, an anode disposed on the substrate, an organic light-emitting layer disposed on the anode, an electron transport layer disposed on the organic light-emitting layer, and a cathode disposed on the electron transport layer. During operation, holes from the anode and electrons from the cathode are emitted to the organic light-emitting layer, and these electrons and holes are combined to generate an excited electron-hole pairs, and the excited electron-hole pairs are converted from an excited state to a ground state to achieve light emitting.

In OLEDs, a dominant luminescent guest material is critical. Guest luminescent materials for early OLEDs are fluorescent materials. Because the ratio of excitons in a singlet energy state and excitons in a triplet energy state in the OLED is 1:3, the theoretical internal quantum efficiency (IQE) of fluorescent-based OLEDs can merely reach 25%, thus considerably limiting the application of fluorescent electroluminescent devices. Heavy metal complex phosphorescent materials can achieve 100% IQE by using the excitons in the singlet energy state and the excitons in the triplet energy state due to a spin-orbit coupling of heavy atoms. However, heavy metals commonly employed are precious metals, such as Ir, Pt, and the like, and the heavy metal complex phosphorescent materials have yet to be developed in fields of blue light materials.

Through a molecular design, pure organic thermally activated delayed fluorescence (TADF) materials can have a small minimum energy state difference ($\Delta E_{ST}$) between the singlet energy state and the triplet energy state, so that the excitons in the triplet energy state can be returned by reverse intersystem crossing (RISC) back to the singlet energy state, then to a ground state by a radiation transition to emit light, and thereby simultaneously use the excitons in the singlet energy state and in the triplet energy state, and 100% IQE may also be achieved.

For TADF materials, since the lifetime of their excitons in triplet energy state is usually from a few microseconds to tens of microseconds, resulting in the quenching effect between the excitons in triplet energy, and thus the efficiency of a TADF luminescent material-based device has severe roll-off. In order to suppress the roll-off of the efficiency of the device, the quenching of the excitons in triplet energy is suppressed by doping of a host and a guest, that is, the distance between the TADF molecules is increased to suppress the quenching of the excitons in triplet energy. Further, the TADF molecule is composed of an electron donor (D) and an electron acceptor (A), and both the electron donor (D) and the electron acceptor (A) are rigid aromatic structures, resulting in relatively poor solubility. A common way to increase the solubility is to add groups of high solubility to the donor, which may lead to difficulties in molecular synthesis and affect molecular properties. In addition, TADF materials have problems such as glass transition temperature (Tg) and thermal decomposition temperature (Td) that affect a service life of the device.

Accordingly, there is an urgent need to develop a thermally activated delayed fluorescent (TADF) material to prepare a TADF organic light emitting diode (OLED) of high performance.

SUMMARY OF INVENTION

To achieve the above object, the present invention provides a thermal activated delayed fluorescent material, including a compound consisting of a receptor A and a donor D, the compound having a molecular structure of D-A shown in Formula 1: D-A, wherein the receptor A is selected from any one of the following structural formulas:

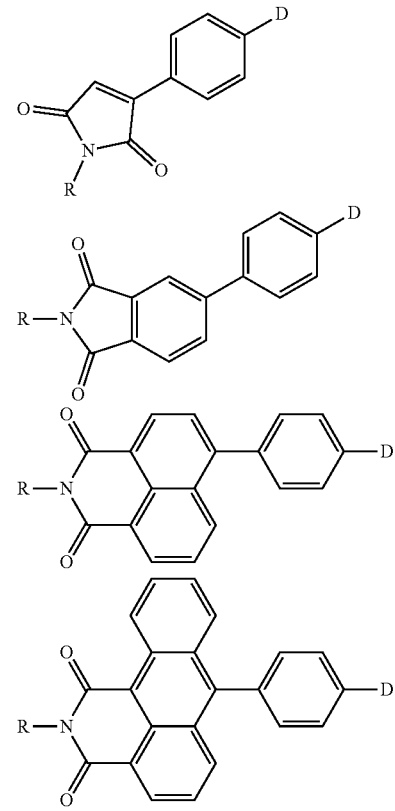

wherein R is selected from any one of the following structural formulas, wherein a dash line represents a bond connecting the R group to the receptor A:

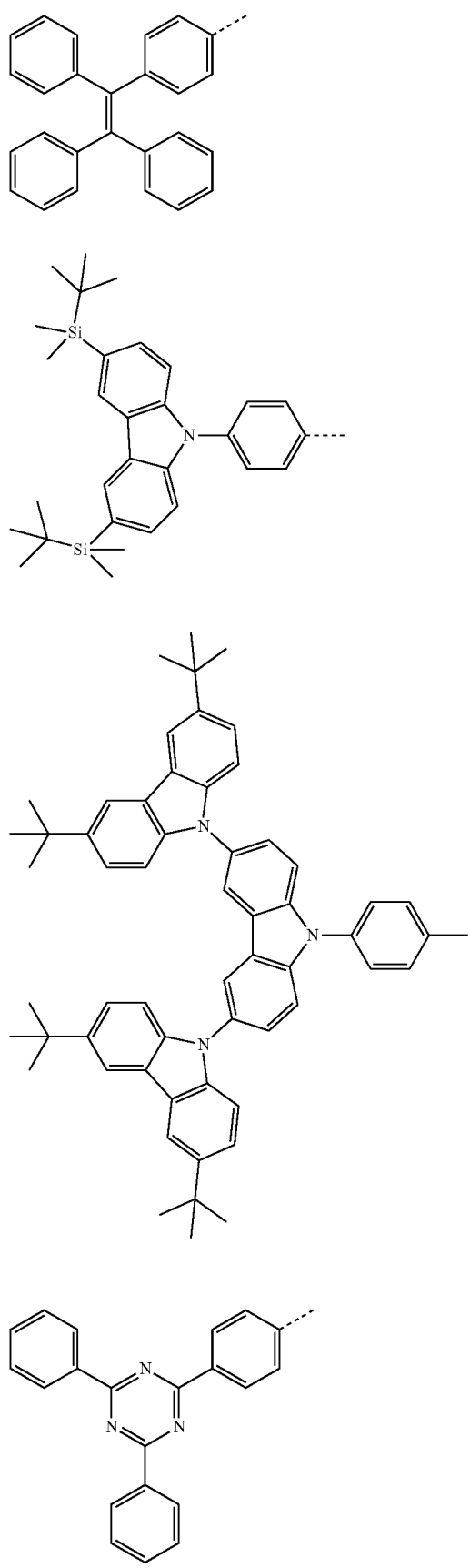
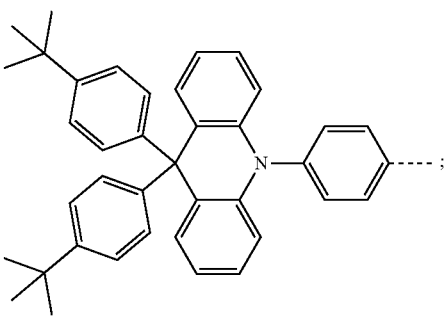
and
wherein the donor D is selected from any one of the following structural formulas:
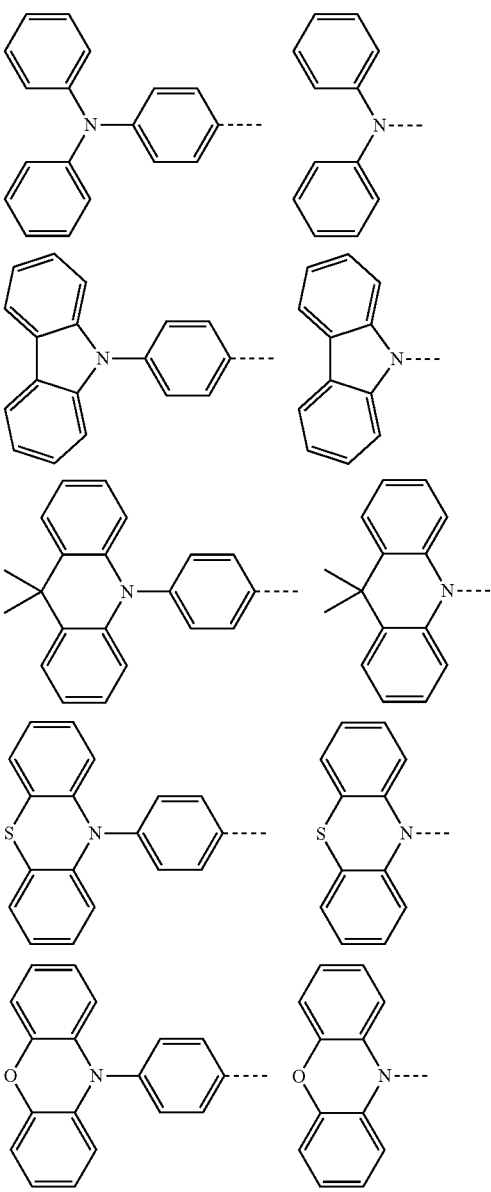

-continued

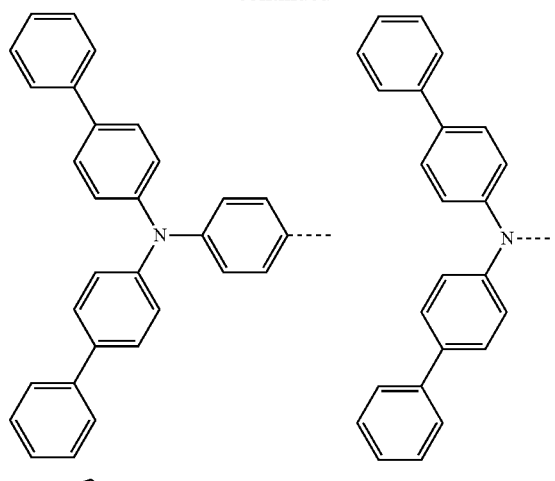

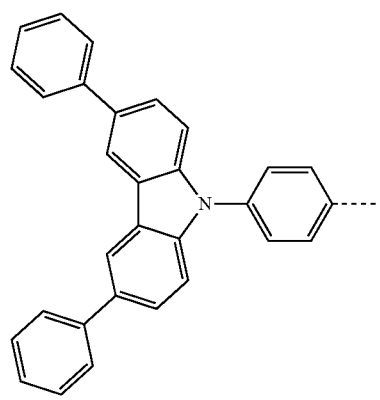

-continued

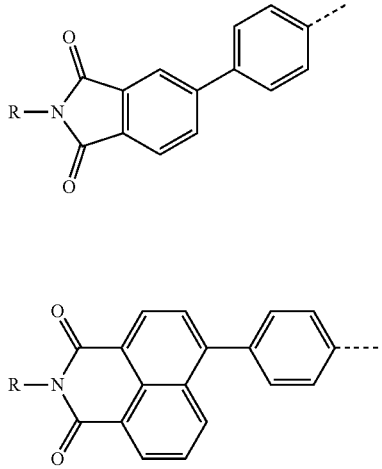

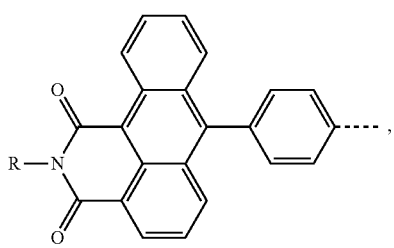

where R is selected from any one of the following structural formulas, wherein a dash line represents a bond connecting the R group to the receptor A:

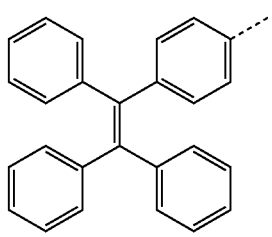

The invention also provides method of preparing a thermal activated delayed fluorescent material, including the following steps:

Step S10, adding a compound A-X and a compound D-H to a solution containing an alkali, wherein X is a halogen, and A is any one of the following structural formulas:

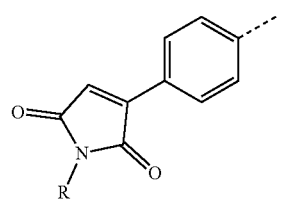

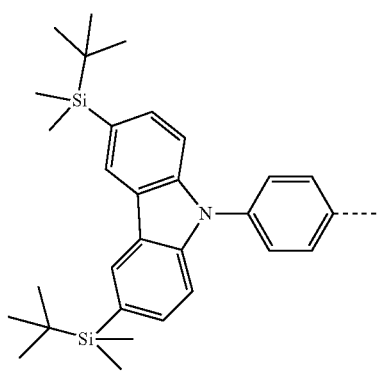

-continued
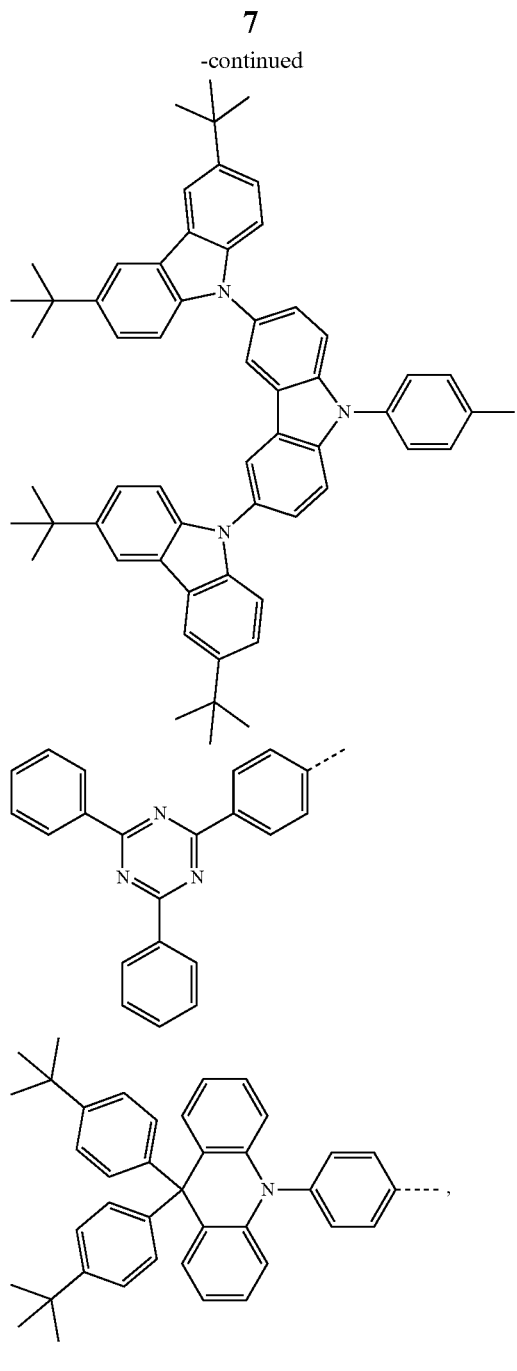
and D is any one of the following structural formulas:
D
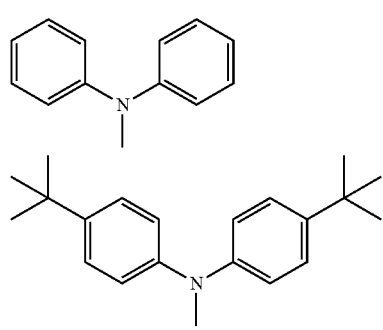
-continued
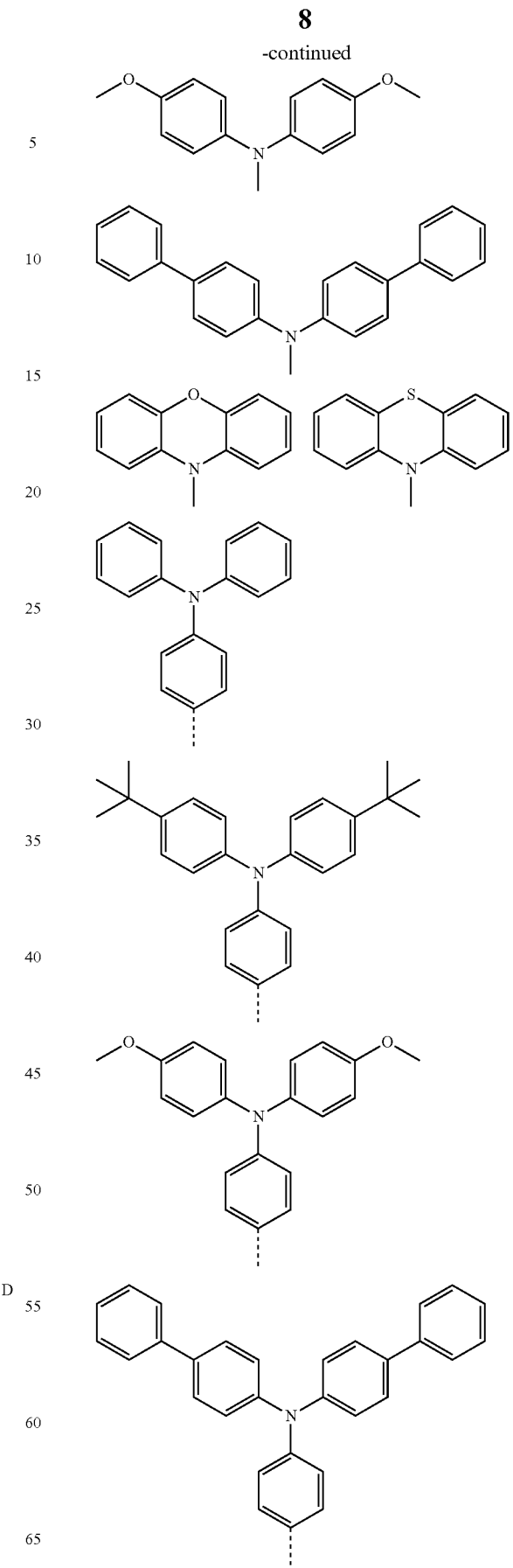

-continued

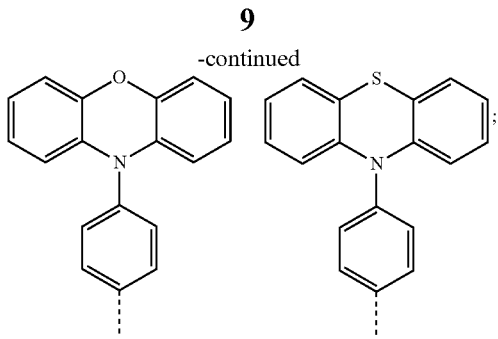

Step S20, adding a palladium catalyst to the solution containing the alkali under an inert gas for reaction at a first temperature for a first period of time to obtain a reaction solution;

Step S30, cooling the reaction solution to a second temperature to obtain a mixture;

Step S40, separating the thermal activated delayed fluorescent material from the mixture, wherein the thermal activated delayed fluorescent material includes a compound consisting of a receptor A and a donor D, the compound having a molecular structure shown in Formula 1: D-A.

According to an embodiment of the invention, in the method of preparing the thermal activated delayed fluorescent material, the first temperature is 80° C.; and the second temperature is room temperature.

According to an embodiment of the invention, in the method of preparing the thermal activated delayed fluorescent material, the first period of time ranges from 12 hours to 36 hours.

According to an embodiment of the invention, in the method of preparing the thermal activated delayed fluorescent material, in the step S10, the solution containing the alkali is tetrahydrofuran and the alkali is sodium carbonate.

According to an embodiment of the invention, in the method of preparing the thermal activated delayed fluorescent material, the step S30 further includes extracting, water washing, dehydrating, filtering, and centrifugal drying the reaction solution to obtain the mixture.

According to an embodiment of the invention, in the method of preparing the thermal activated delayed fluorescent material, the step S40 is performed by column chromatography, and the eluent used in the column chromatography is petroleum ether and dichloromethane in a volume ratio of 1:2.

According to an embodiment of the invention, in the method of preparing the thermal activated delayed fluorescent material, the compound A-X is 6-bromo-2-(4-(1,2,2-triphenylvinyl)phenyl)-benzene[de]isoquinoline-1,3-dione, and the compound D-H is phenothiazine.

The invention further provides an electroluminescent device including: a substrate layer; a hole injection layer disposed on the substrate layer; a hole transport layer disposed on the hole injection layer; a light emitting layer disposed on the hole transport layer; an electron transport layer disposed on the light emitting layer; and a cathode layer disposed on the electron transport layer, wherein the light emitting layer includes the thermal activated delayed fluorescent material.

According to an embodiment of the invention, in the electroluminescent device, the base layer is made of material including ITO; the hole injection layer is made of material including 2,3,6,7,10,11-hexacyano-1,4,5,8,9,12-hexaazatriphenylene; the hole transport layer is made of material including 4,4'-cyclohexyl bis[N,N-bis(4-methylphenyl)aniline]; the electron transport layer is made of material including 1,3,5-tris(3-(3-pyridyl)phenyl)benzene; and the cathode layer is made of material including lithium fluoride and aluminum.

An object of the present invention is to provide a thermally activated delayed fluorescent (TADF) material, wherein a series of thermally activated delayed fluorescent molecules containing imide acceptors are synthesized through a sophisticated molecular design. By functionally modifying a nitrogen atom of the imide structure, for example, introducing a tetraphenylvinyl group having aggregation-induced enhanced luminescence (AIEE) and a silicon-containing group of large sterically hindered group, a non-doped device of high efficiency can be achieved. Alternately, electron or hole mobility of the TADF molecule can be adjusted by introducing an electron donor or an electron acceptor, or Tg and Td of the TADF molecule can be adjusted by introducing a group, to realize preparation of a series of TADF organic light emitting diodes (OLEDs) of high performance using these luminescent materials.

BRIEF DESCRIPTION OF DRAWINGS

In order to more clearly illustrate the embodiments or the technical solutions of the existing art, the drawings illustrating the embodiments or the existing art will be briefly described below. Obviously, the drawings in the following description merely illustrate some embodiments of the present invention. Other drawings may also be obtained by those skilled in the art according to these figures without paying creative work.

FIG. 1 is a flow chart showing a method for preparing a thermally activated delayed fluorescent material according to an embodiment of the present invention.

DETAILED DESCRIPTION OF PREFERRED EMBODIMENTS

Figure 2:
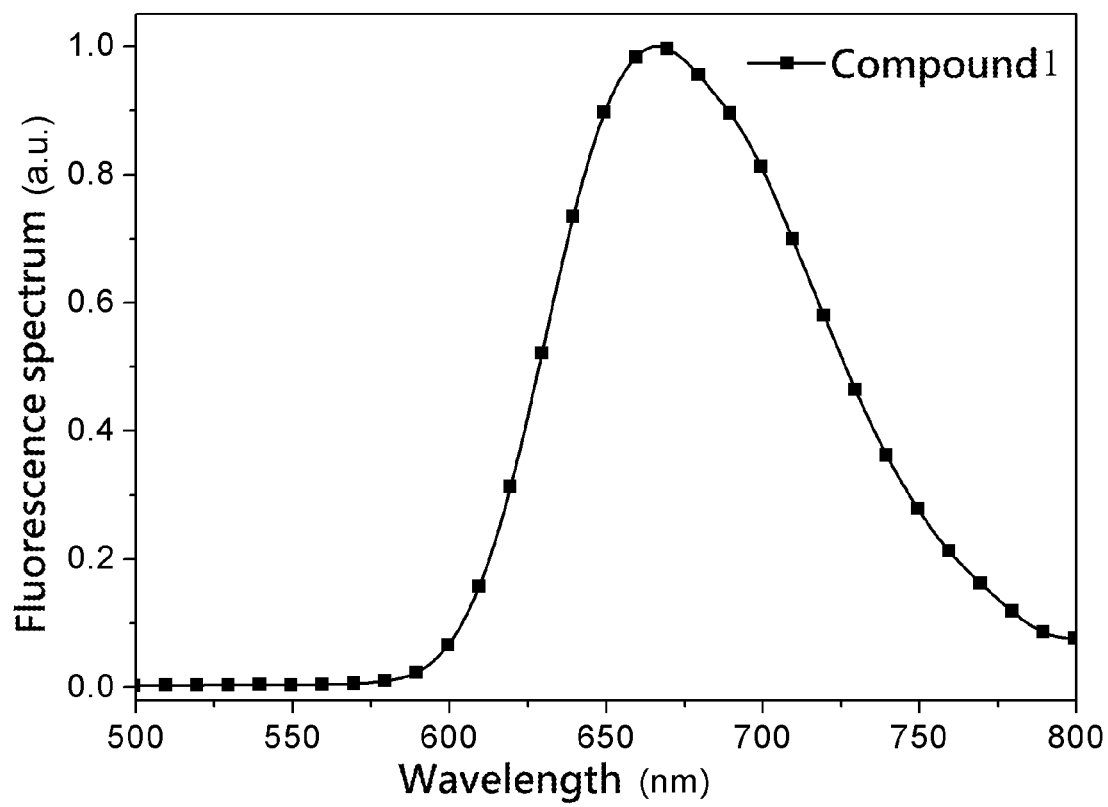
FIG. 2 is a fluorescence emission spectrum of a compound according to an embodiment of the present invention.

Embodiments of the present invention provide a thermally activated delayed fluorescent (TADF) material, wherein a series of thermally activated delayed fluorescent molecules containing imide acceptors are synthesized through a sophisticated molecular design. By functionally modifying a nitrogen atom of the imide structure, for example, introducing a tetraphenylvinyl group having aggregation-induced enhanced luminescence (AIEE) and a silicon-containing group of large sterically hindered group, a non-doped device of high efficiency can be achieved. Alternately, electron or hole mobility of the TADF molecule can be adjusted by introducing an electron donor or an electron acceptor, or Tg and Td of the TADF molecule can be adjusted by introducing a group, to realize preparation of a series of TADF organic light emitting diodes (OLEDs) of high performance using these luminescent materials.

To achieve the above object, the present invention provides a thermal activated delayed fluorescent material, including a compound consisting of a receptor A and a donor D, the compound having a molecular structure of D-A shown in Formula 1:

D-A          Formula 1 wherein the receptor A is selected from any one of the following structural formulas:
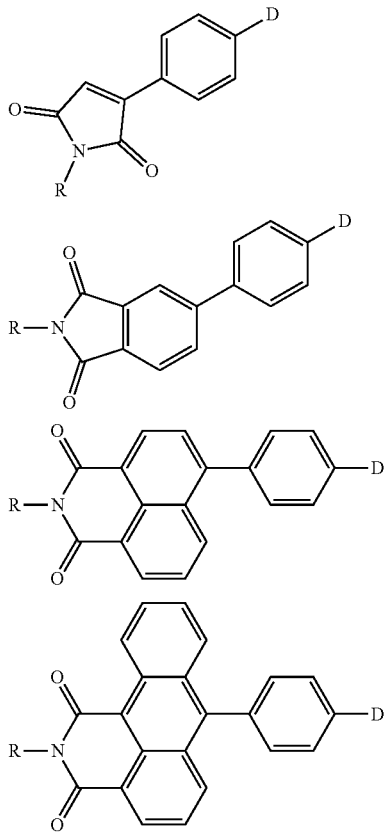
wherein R is selected from any one of the following structural formulas, wherein a dash line represents a bond connecting the R group to the receptor A:
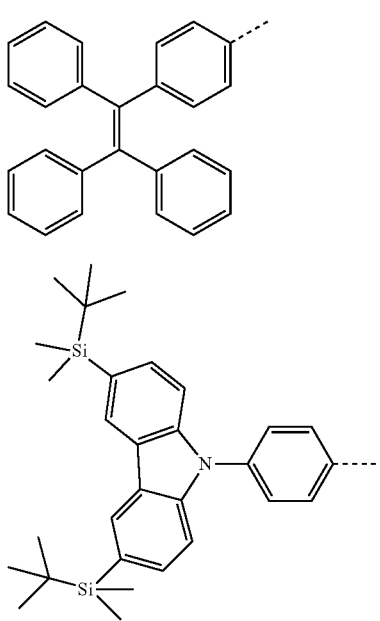
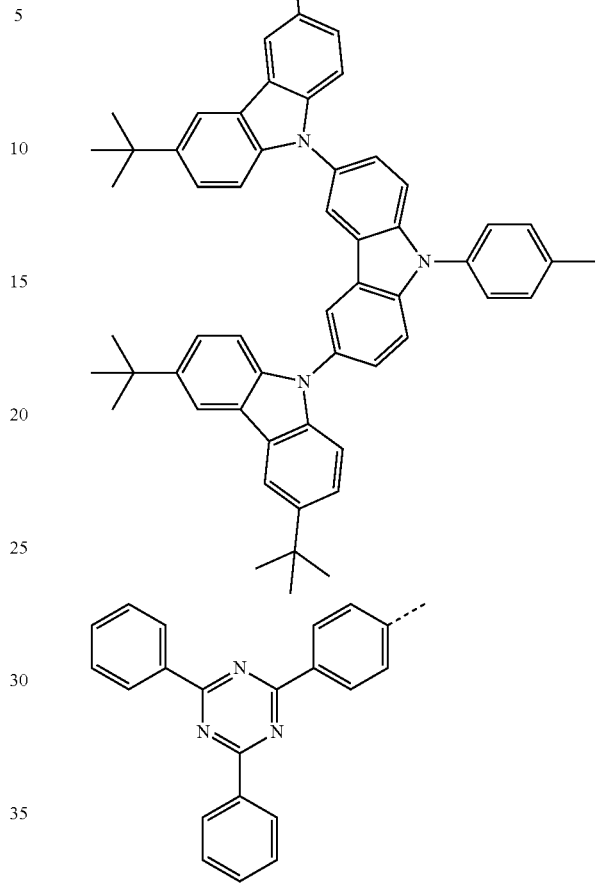
and
wherein the donor D is selected from any one of the following structural formulas:
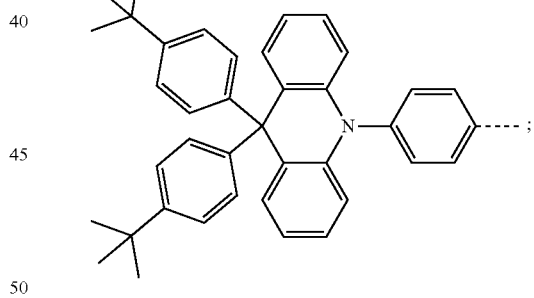

-continued

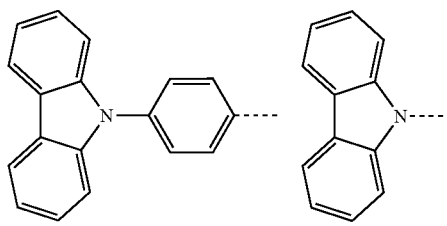

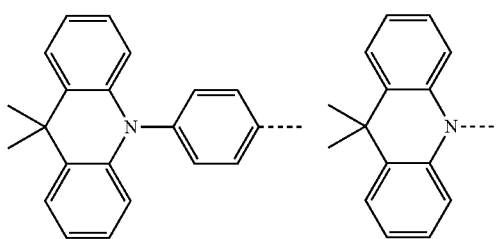

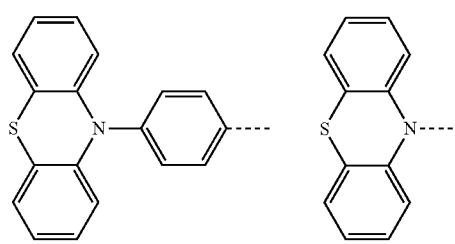

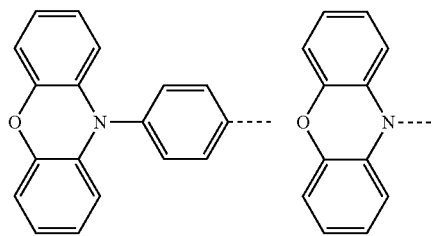

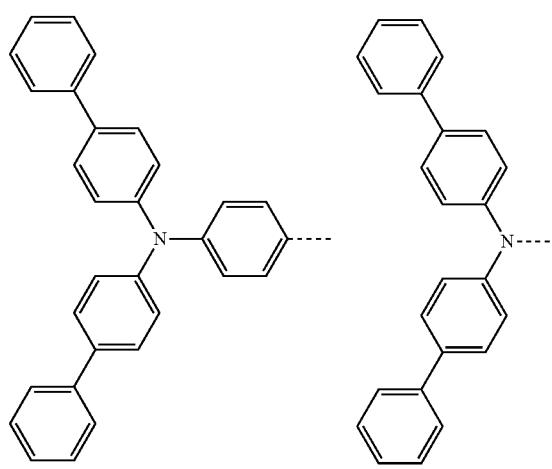

-continued

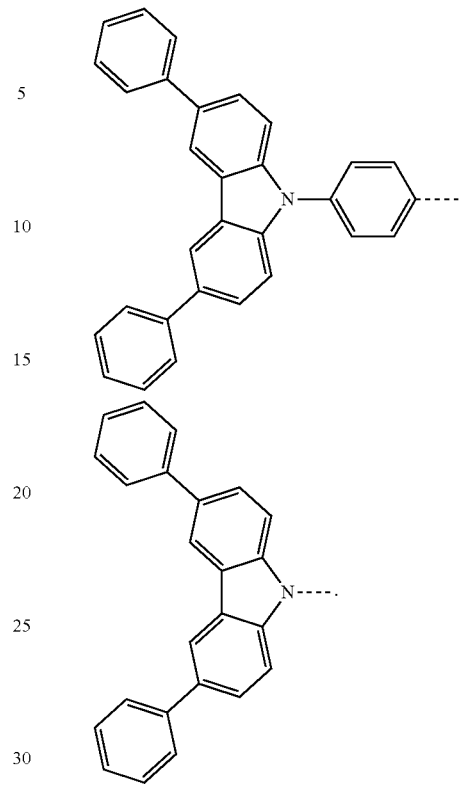

Referring to FIG. 1, FIG. 1 is a flow chart showing a method for preparing a thermally activated delayed fluorescent material according to an embodiment of the present invention. As shown in FIG. 1, the method for preparing a thermally activated delayed fluorescence (TADF) material according to an embodiment of the present invention includes the following steps:

Step S10, adding a compound A-X and a compound D-H to a solution containing an alkali, wherein X is a halogen, and A is any one of the following structural formulas:

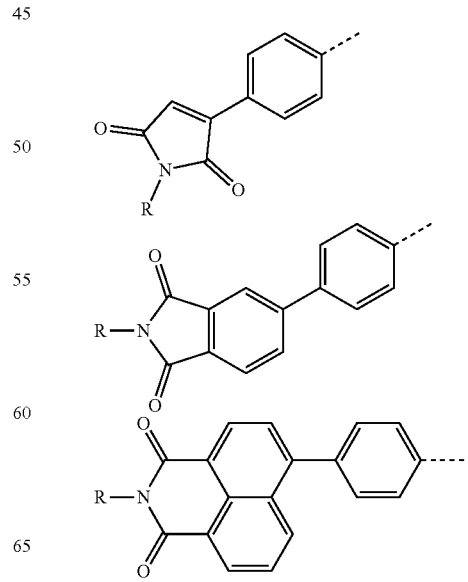

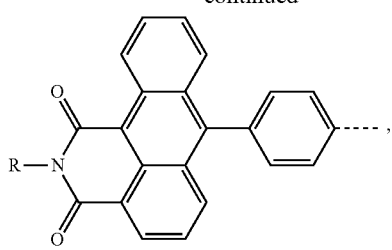
where R is selected from any one of the following structural formulas, wherein a dash line represents a bond connecting the R group to the receptor A:
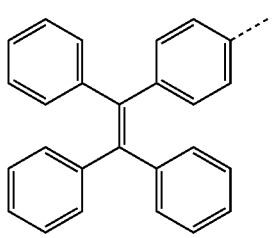
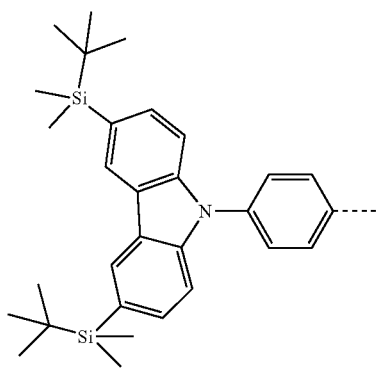
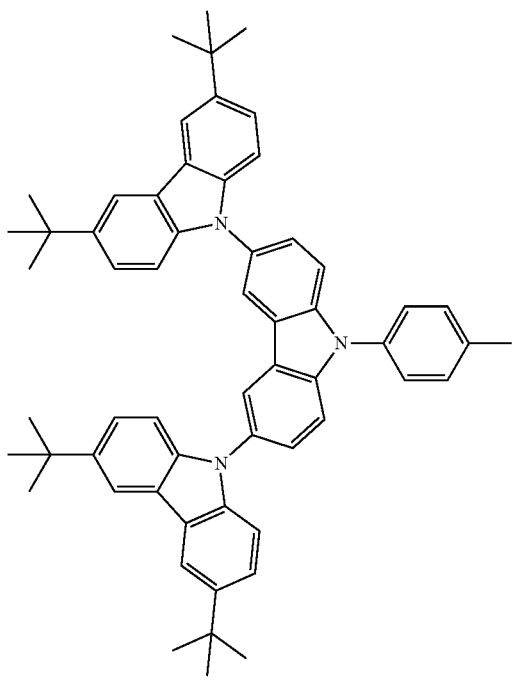
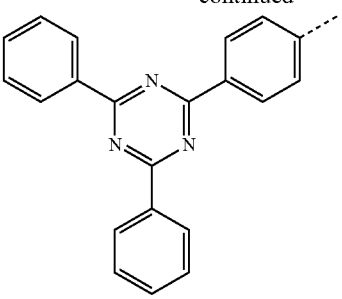
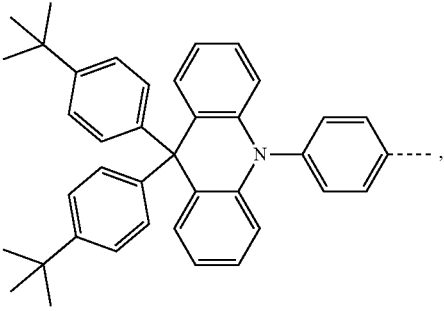
and D is any one of the following structural formulas:
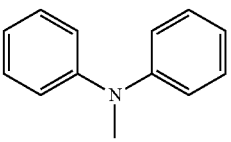
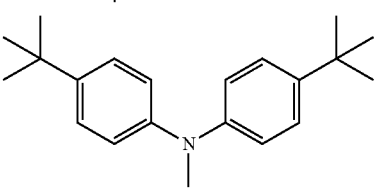
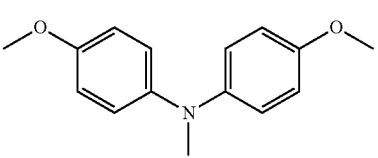
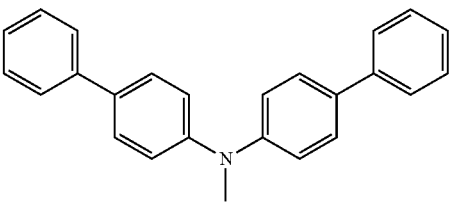
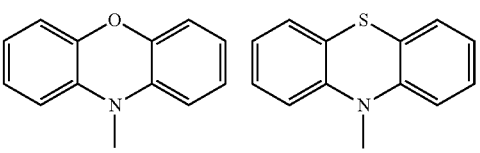

-continued

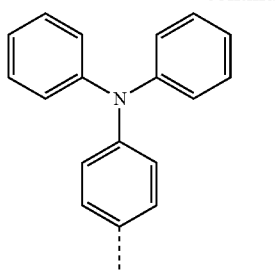

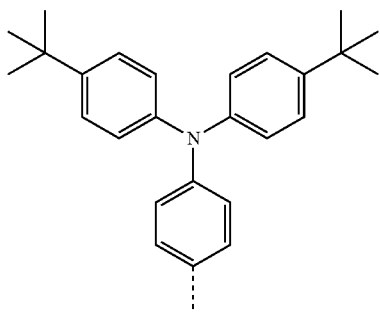

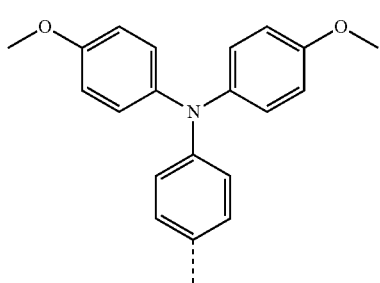

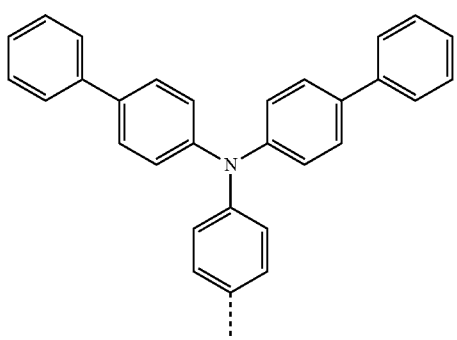

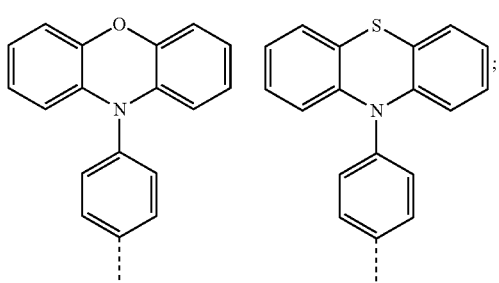

Step S20, adding a palladium catalyst to the solution containing the alkali under an inert gas for reaction at a first temperature for a first period of time to obtain a reaction solution;

Step S30, cooling the reaction solution to a second temperature to obtain a mixture;

Step S40, separating the thermal activated delayed fluorescent material from the mixture, wherein the thermal activated delayed fluorescent material includes a compound consisting of a receptor A and a donor D, the compound having a molecular structure shown in Formula 1:

D-A  Formula 1.

According to an embodiment of the invention, in the method of preparing the thermal activated delayed fluorescent material, the first temperature is 80° C.; and the second temperature is room temperature.

According to an embodiment of the invention, in the method of preparing the thermal activated delayed fluorescent material, the first period of time ranges from 12 hours to 36 hours.

According to an embodiment of the invention, in the method of preparing the thermal activated delayed fluorescent material, in the step S10, the solution containing the alkali is tetrahydrofuran and the alkali is sodium carbonate.

According to an embodiment of the invention, in the method of preparing the thermal activated delayed fluorescent material, the step S30 further includes extracting, water washing, dehydrating, filtrating, and centrifugal drying the reaction solution to obtain the mixture.

According to an embodiment of the invention, in the method of preparing the thermal activated delayed fluorescent material, the step S40 is performed by column chromatography, and the eluent used in the column chromatography is petroleum ether and dichloromethane in a volume ratio of 1:2.

According to an embodiment of the invention, in the method of preparing the thermal activated delayed fluorescent material, the compound A-X is 6-bromo-2-(4-(1,2,2-triphenylvinyl)phenyl)-benzene[de]isoquinoline-1,3-dione, and the compound D-H is phenothiazine.

EXAMPLE 1

In the specific Example 1 of the present invention, a thermal activation delayed fluorescent material was provided, which was a target compound having a molecular structure shown in Formula 2:

Formula 2

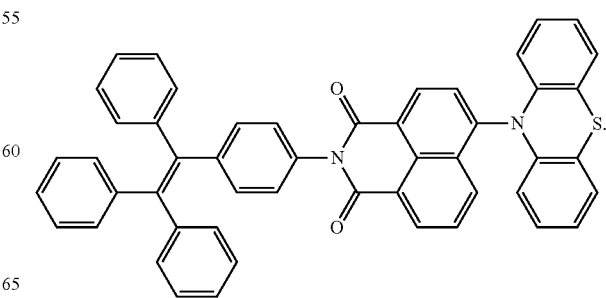

The target compound having a molecular structure of Formula 2 was synthesized by a reaction based on a synthetic route shown in Reaction Scheme 1:

Reaction formula 1

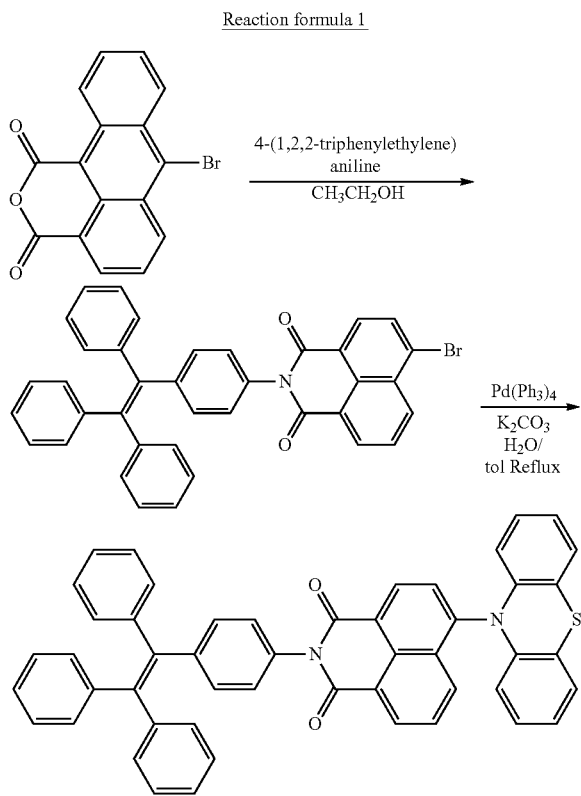

The detailed synthesis steps of Compound 1 are as follows:

7-Bromophenyl [de,h]isobenzopyran-1,3-dione (3.27 g, 10 mmol), 4-(1,2,2-triphenylethylene)aniline (3.47 g, 10 mmol, and ethanol (20 mL) were added to a 100 mL schlenk bottle, for reaction under argon gas atmosphere by heating to reflux overnight. After the reaction solution was cooled to room temperature, the reaction solution was extracted three times with dichloromethane (DCM), followed by washing three times with water, then dried over anhydrous sodium sulfate, and then filtered and spin-dried. The crude product was chromatographed by a 200-300 mesh silica gel column and eluted with DCM:EtOAc (V/V=1:2). After that, the product was rotary-evaporated and dried in vacuum to obtain a yellow solid (4.96 g, 82% yield). HRMS [M+H]+ calcd. for C38H24BrNO2: 605.0990; found: 605.1003.

6-Bromo-2-(4-(1,2,2-triphenylvinyl)phenyl)-phenyl[de]isoquinoline-1,3 -dione (3.03 g, 5 mmol), phenothiazine azine (1.09 g, 5.5 mmol), 100 mL of tetrahydrofuran and 25 mL of a 1.6 M sodium carbonate solution were placed in a 250 mL three-necked flask, and purged with argon gas. Then, tetrakis(triphenylphosphine)palladium (0.24 g, 0.2 mmol) was added, and the mixture was refluxed at 80° C. for 24 h. After the reaction solution was cooled to room temperature, it was extracted three times with DCM, then washed three times, followed by drying over anhydrous sodium sulfate, and then filtered and spin-dried.

Column chromatography was carried out by a 200-300 mesh silica gel column with an eluent of petroleum ether: DCM (1:2, V/V) to obtain 2.97 g of a red solid, and yield was 82%. HRMS [M+H]+ calcd. for C50H32N2SO2: 724.2184; found: 724.2198.

Specifically, Compound 1 was defined to have the molecular structure shown in Formula 2. Compound 1 was examined, and the fluorescence emission spectrum of Compound 1 under a pure film is shown in FIG. 2

The characteristic parameters of lowest singlet state (S100), lowest triplet energy level (T1), and photoluminescence quantum yield (PLQY) of Compound 1 were analyzed based on B3LYP theory, and the analysis results are shown in Table 1.

TABLE 1

| Compound | PL Peak (nm) | S100 (eV) | $T_1$ (eV) | $\Delta E_{ST}$ (eV) | PLQY (%) |
|---|---|---|---|---|---|
| Compound 1 | 667 | 2.05 | 1.91 | 0.14 | 87 |

PL peak is the photoluminescence peak, S100 is the lowest singlet energy level, T1 is the lowest triplet energy level, and ΔEST is the energy level difference between the lowest singlet energy level and the lowest triplet energy level.

As can be known from FIG. 2 and Table 1, Compound 1 of Example 1 of the present invention satisfies the performance requirements.

Furthermore, an embodiment of the present invention also provides an electroluminescent device including the above-described thermally activated delayed fluorescent (TADF) material.

Figure 3:
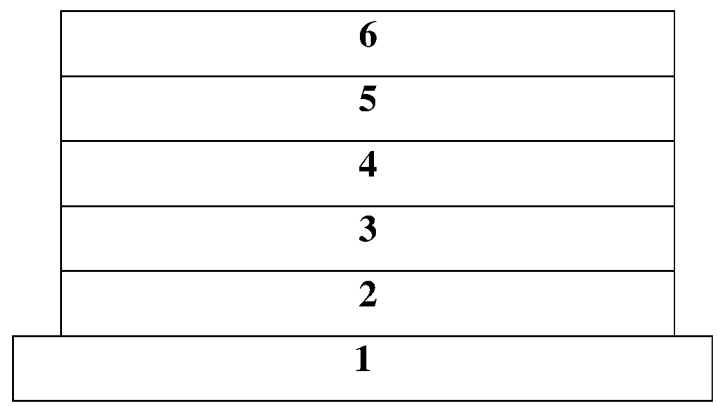
FIG. 3 is a schematic structural diagram of an electroluminescent device according to an embodiment of the invention.

Referring to FIG. 3, in particular, the electroluminescent device 100 includes: a substrate layer 1; a hole injection layer 2 disposed on the substrate layer 1; a hole transport layer 3 disposed on the hole injection layer 2; a light emitting layer 4 disposed on the hole transport layer 3; an electron transport layer 5 disposed on the light emitting layer 4; and a cathode layer 6 disposed on the electron transport layer 5, wherein the light emitting layer 4 includes the thermal activated delayed fluorescent (TADF) material.

According to an embodiment of the invention, in the electroluminescent device, the base layer is made of material including ITO; the hole injection layer is made of material including 2,3,6,7,10,11-hexacyano-1,4,5,8,9,12-hexaazatriphenylene; the hole transport layer is made of material including 4,4'-cyclohexyl bis[N,N-bis(4-methylphenyl)aniline]; the electron transport layer is made of material including 1,3,5-tris(3-(3-pyridyl)phenyl)benzene; and the cathode layer is made of material including lithium fluoride and aluminum.

Specifically, the device 100 was fabricated using Compound 1 as the light-emitting layer 4, and the performance of the device 100 was measured. The substrate layer 1 and the hole injection layer 2 in the device 100 had a thickness of 30 nm. The hole transport layer 3 had a thickness of 40 nm. The light-emitting layer 4 of the device 100 had a thickness of 40 nm. The electron transport layer 5 had a thickness of 40 nm. In the cathode 5, the lithium fluoride in the cathode 500 had a thickness of 1 nm, and the aluminum had a thickness of 100 nm.

The current-brightness-voltage characteristics of the device 100 was further measured by a Keithley source measurement system (Keithley 2400 Sourcemeter, Keithley 2000 Currentmeter) with a calibrated silicon photodiode.

The electroluminescence spectrum was measured by a French JY SPEX CCD3000 spectrometer. All measurements were conducted at room temperature under ambient atmosphere. The performance data of the device 100 is shown in Table 2 below, and the device 100 meets the performance requirements.

TABLE 2

| Device 1 | maximum brightness (cd/m$^2$) | EL peak (nm) | maximum external quantum efficiency (%) |
|---|---|---|---|
| Compound 1 | 1395 | 679 | 15 |

Accordingly, embodiments of the present invention provide a thermally activated delayed fluorescent (TADF) material, wherein a series of thermally activated delayed fluorescent molecules containing imide acceptors are synthesized through a sophisticated molecular design. By functionally modifying a nitrogen atom of the imide structure, for example, introducing a tetraphenylvinyl group having aggregation-induced enhanced luminescence (AIEE) and a silicon-containing group of large sterically hindered group, a non-doped device of high efficiency can be achieved. Alternately, electron or hole mobility of the TADF molecule can be adjusted by introducing an electron donor or an electron acceptor, or Tg and Td of the TADF molecule can be adjusted by introducing a group, to realize preparation of a series of TADF organic light emitting diodes (OLEDs) of high performance using these luminescent materials.

While the present invention has been described by way of example and in terms of the preferred embodiments, it is to be understood that the present invention is not limited to the disclosed embodiments. To the contrary, it is intended to cover various modifications and similar arrangements. Therefore, the scope of the appended claims should be accorded the broadest interpretation so as to encompass all such modifications and similar arrangements.

What is claimed is:

1. A thermal activated delayed fluorescent material, comprising a compound consisting of a receptor A and a donor D, the compound having a molecular structure of D-A shown in Formula 1:

D-A                Formula 1 wherein the receptor A is selected from any one of the following structural formulas:

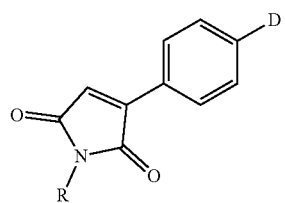

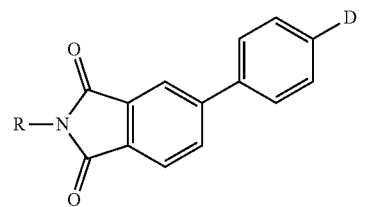

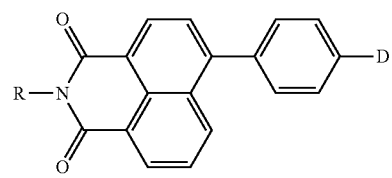

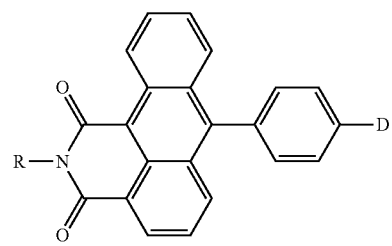

wherein R is selected from any one of the following structural formulas, wherein a dash line represents a bond connecting the R group to the receptor A:

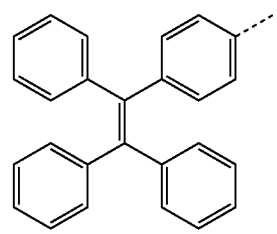

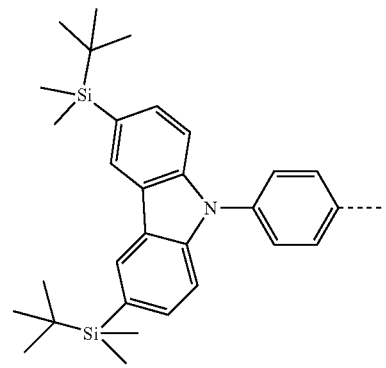

-continued
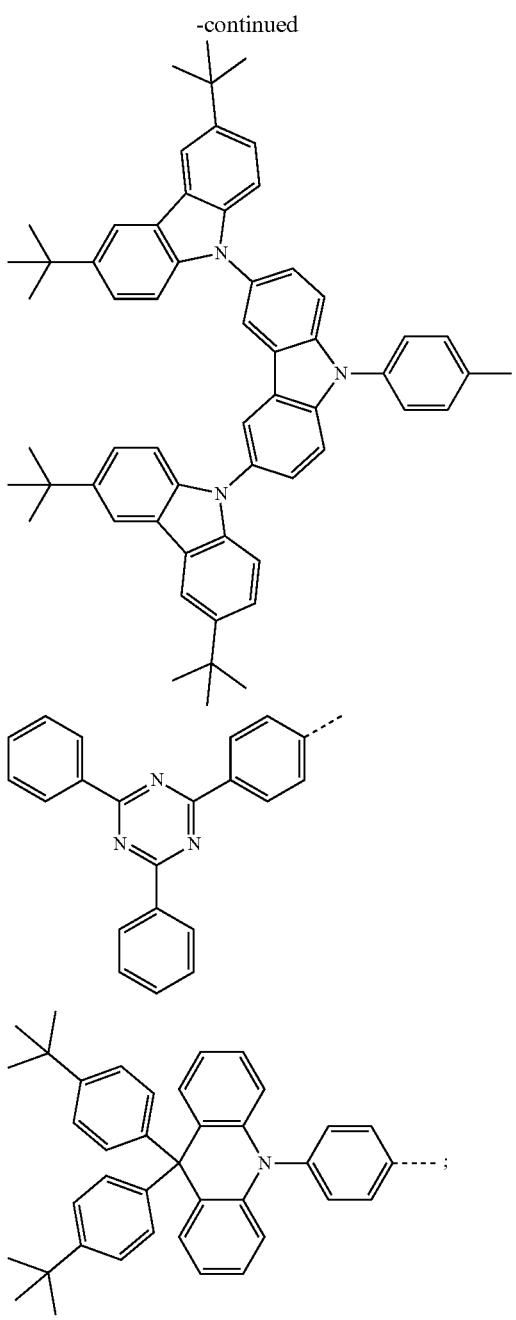
and
wherein the donor D is selected from any one of the following structural formulas:
D
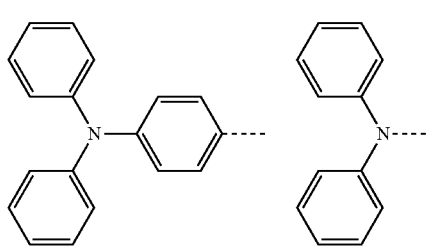
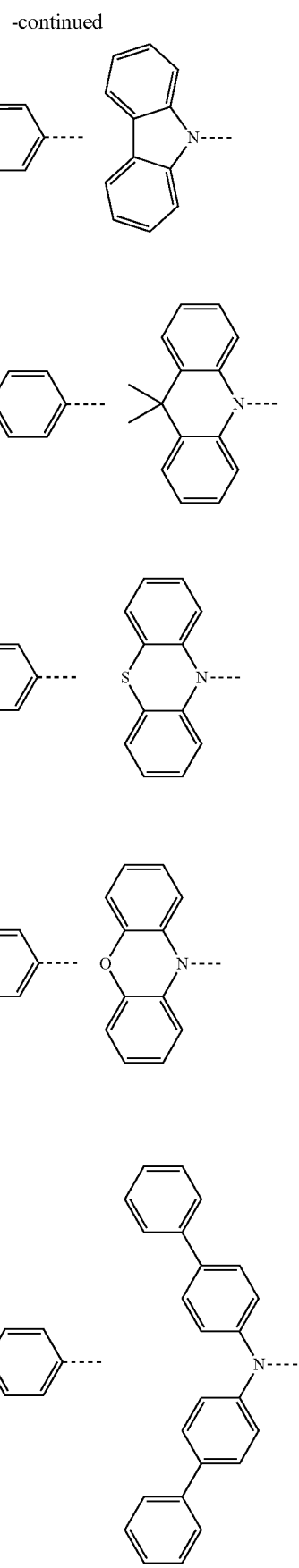

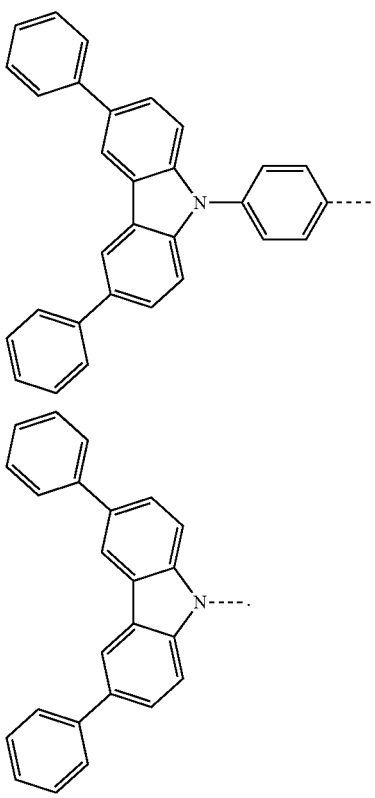

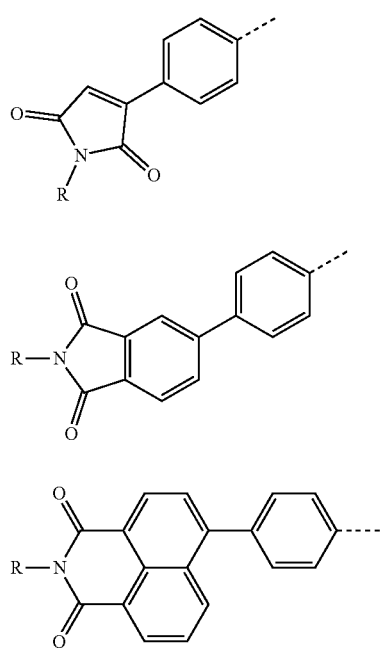

2. A method of preparing a thermal activated delayed fluorescent material, comprising the following steps:

Step S10, adding a compound A-X and a compound D-H to a solution containing an alkali, wherein X is a halogen, and A is any one of the following structural formulas:

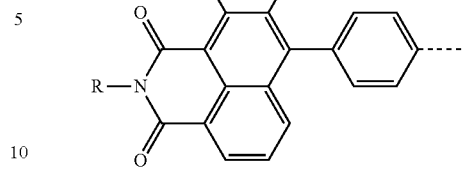

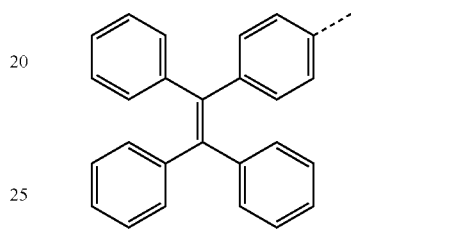

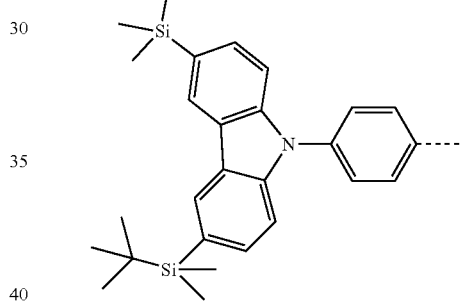

where R is selected from any one of the following structural formulas, wherein a dash line represents a bond connecting the R group to the receptor A:

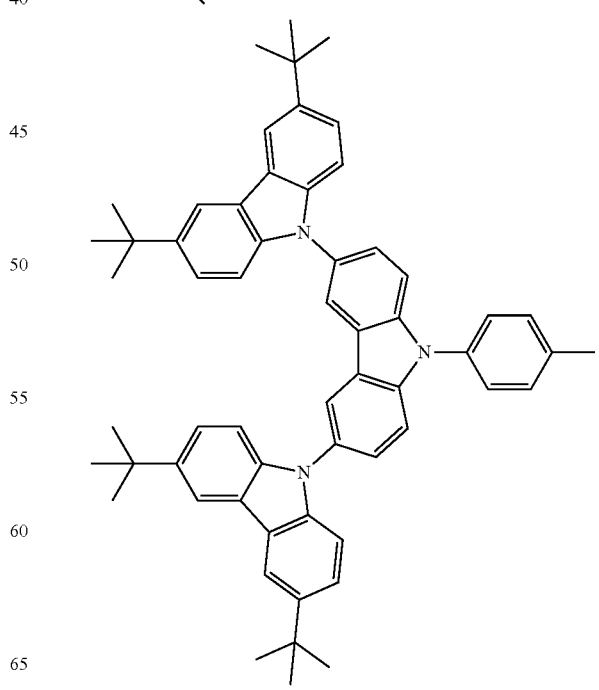

-continued

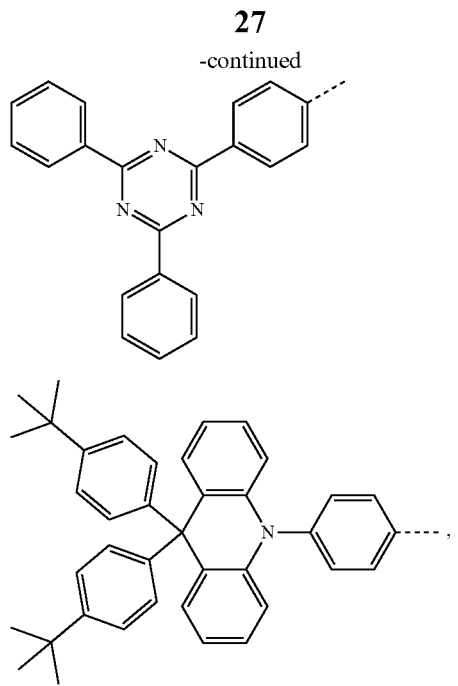

and D is any one of the following structural formulas:

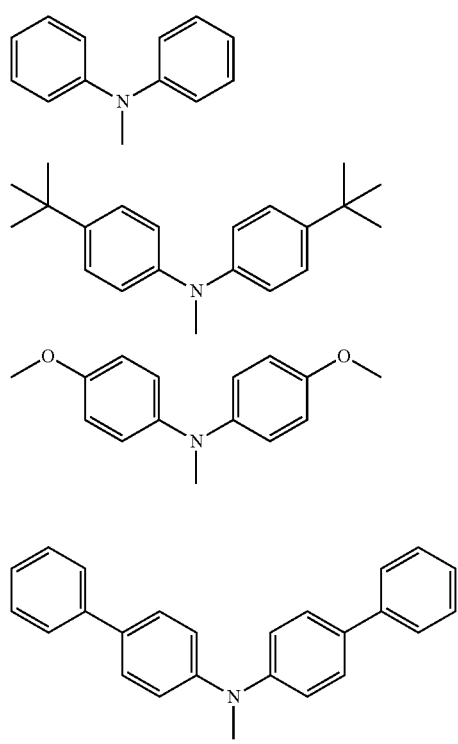

-continued

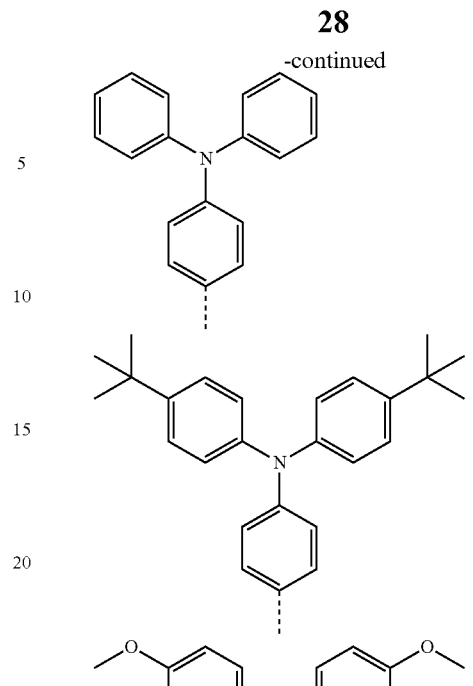

D

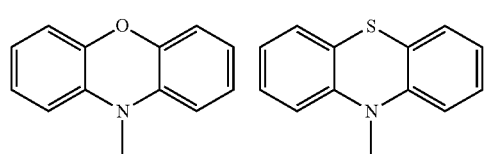

Step S20, adding a palladium catalyst to the solution containing the alkali under an inert gas for reaction at a first temperature for a first period of time to obtain a reaction solution;

Step S30, cooling the reaction solution to a second temperature to obtain a mixture;

Step S40, separating the thermal activated delayed fluorescent material from the mixture, wherein the thermal activated delayed fluorescent material comprises a compound consisting of a receptor A and a donor D, the compound having a molecular structure shown in Formula 1:

D-A    Formula 1.

3. The method of preparing the thermal activated delayed fluorescent material according to claim 2, wherein the first temperature is 80° C.; and the second temperature is room temperature.

4. The method of preparing the thermal activated delayed fluorescent material according to claim 2, wherein the first period of time ranges from 12 hours to 36 hours.

5. The method of preparing the thermal activated delayed fluorescent material according to claim 2, wherein in the step S10, the solution containing the alkali is tetrahydrofuran and the alkali is sodium carbonate.

6. The method of preparing the thermal activated delayed fluorescent material according to claim 2, wherein the step S30 further comprises extracting, water washing, dehydrating, filtrating, and centrifugal drying the reaction solution to obtain the mixture.

7. The method of preparing the thermal activated delayed fluorescent material according to claim 2, wherein the step S40 is performed by column chromatography, and the eluent used in the column chromatography is petroleum ether and dichloromethane in a volume ratio of 1:2.

8. The method of preparing the thermal activated delayed fluorescent material according to claim 2, wherein the compound A-X is 6-bromo-2-(4-(1,2,2-triphenylvinyl)phenyl)-benzene[de]isoquinoline-1,3-dione, and the compound D-H is phenothiazine.

9. An electroluminescent device, comprising:
a substrate layer;
a hole injection layer disposed on the substrate layer;
a hole transport layer disposed on the hole injection layer;
a light emitting layer disposed on the hole transport layer;
an electron transport layer disposed on the light emitting layer; and
a cathode layer disposed on the electron transport layer,
wherein the light emitting layer comprises the thermal activated delayed fluorescent material of claim 1.

10. The electroluminescent device according to claim 9, wherein:
the base layer is made of material comprising ITO;
the hole injection layer is made of material comprising 2,3,6,7,10,11-hexacyano-1,4,5,8,9,12-hexaazatriphenylene;
the hole transport layer is made of material comprising 4,4'-cyclohexyl bis[N,N-bis(4-methylphenyl)aniline];
the electron transport layer is made of material comprising 1,3,5-tris(3-(3-pyridyl)phenyl)benzene; and
the cathode layer is made of material comprising lithium fluoride and aluminum.

* * * * *